(12) United States Patent
Taylor et al.

(10) Patent No.: US 6,561,046 B1
(45) Date of Patent: May 13, 2003

(54) SAMPLING APPARATUS FOR COLLECTING SAMPLES FROM UNDERWATER HYDROTHERMAL VENTS AND THE MARINE OR LIMNOLOGICAL WATER COLUMN

(75) Inventors: Craig D. Taylor, Mashpee, MA (US); Kenneth W. Doherty, Falmouth, MA (US)

(73) Assignee: McLane Research Laboratories, Falmouth, MA (US)

( * ) Notice: Subject to any disclaimer, the term of this patent is extended or adjusted under 35 U.S.C. 154(b) by 259 days.

(21) Appl. No.: 09/689,371

(22) Filed: Oct. 12, 2000

(51) Int. Cl.⁷ ................................................. G01N 1/00
(52) U.S. Cl. .................................. 73/863.23; 73/863.33
(58) Field of Search ......................... 73/863.01, 863.11, 73/863.21, 863.23, 863.31, 863.33, 864.31, 864.34, 864.35, 864.73

(56) References Cited

U.S. PATENT DOCUMENTS

| | | | |
|---|---|---|---|
| 4,163,392 A | * 8/1979 | Fleenor et al. | 73/864.35 |
| 4,584,887 A | * 4/1986 | Galen | 73/863.31 |
| 5,029,485 A | * 7/1991 | Marr | 73/864.34 |
| 5,404,760 A | * 4/1995 | Robinson et al. | 73/863.11 |
| 5,463,909 A | * 11/1995 | Eldridge | 73/864.34 |
| 5,553,507 A | * 9/1996 | Basch et al. | 73/863.33 |
| 5,777,241 A | * 7/1998 | Evenson | 73/863.11 |
| 6,192,767 B1 | * 2/2001 | Fiorina | 73/864.34 |

FOREIGN PATENT DOCUMENTS

| | | | | |
|---|---|---|---|---|
| GB | 0917080 | * | 1/1963 | 73/864.34 |

* cited by examiner

Primary Examiner—Robert Raevis
(74) Attorney, Agent, or Firm—William B. Ritchie

(57) ABSTRACT

A sampling apparatus that allows multiple uncontaminated samples to be taken from hydrothermal vents and the oceanic or limnological water column. The apparatus includes a sampling nozzle for taking in the sample. A sample collection unit is in fluid communication with the sampling nozzle and includes at least one sampling module for the collection of a predetermined type of sample. A fluid intake module is in fluid communication with the sample collection unit and the sampling nozzle. The fluid intake module includes at least one pump for drawing a sample fluid through the sampling nozzle and sample collection unit. A control module is in electrical communication with the fluid intake module. The control module includes a micro-controller for controlling the fluid intake module and a computer readable memory for storing sampling data for use by a user. In operation, the sampling nozzle is moved into a desired sampling location and the micro-controller sends a signal to said fluid intake module to initiate collection of a sample. The fluid intake module then draws the sample fluid through said sampling nozzle and into said sample collection unit. The sampling module then stores a sample and the computer readable memory stores the sampling data for use by a user.

19 Claims, 7 Drawing Sheets

SAMPLING APPARATUS FOR COLLECTING SAMPLES FROM UNDERWATER HYDROTHERMAL VENTS AND THE MARINE OR LIMNOLOGICAL WATER COLUMN

FIELD OF THE INVENTION

The present invention relates to an underwater microbial and water sampler and, in particular, to a sampler capable of collecting uncontaminated samples from very hot water when mounted on manned submersibles, Remotely Operated Vehicles (ROV's), Autonomous Underwater Vehicles (AUV's), or ships.

BACKGROUND OF THE INVENTION

Submarine hydrothermal vents are unique ecosystems in which a large biomass of microorganisms and higher life forms are supported by chemosynthetic carbon production based upon the oxidation of geothermally produced reduced forms of sulfur. These habitats subject both macroflora and microflora to steep temperature and chemical gradients. On small scales, the habitat is diverse and microorganisms have evolved novel solutions to an existence in a physically demanding, potentially toxic, transitory and high fluid flow environment. It has been suggested that vent ecosystems are possible models for the evolution of life on earth or in extraterrestrial systems.

The study of the ecology and diversity of microorganisms in aquatic extreme environments, such as hydrothermal vents, requires the marriage between traditional microbial culturing techniques and modem phylogenetic techniques based on DNA sequencing. The role of this invention is to provide samples for these studies that are free from contamination by exogenous microbes and microbial DNA. Microbes typically inhabit the aquatic environment in high numbers. The chances for such contamination are increased due to the necessity for transport of the sampling apparatus through contaminating waters to the site of sampling and because in environments such as hydrothermal vents steep temperature and chemical gradients result in large changes in diversity on small spatial scales.

The distances and extreme temperatures often associated with this task require not only an apparatus that is capable of extracting uncontaminated samples, but also one that may be controlled remotely. It must also withstand these extremes for a sufficient length of time to allow multiple samples to be acquired. Unfortunately, current sampling apparatus are unable to tolerate even transient exposure to the extreme temperatures around these vents, sometimes as high as 400° C., and make no provisions for prevention of contamination from the environment or cross-contamination between samples.

Therefore, there is a need for an apparatus that may extract samples from the aquatic water column and hydrothermal vents, that is capable of withstanding transient exposure to extreme temperatures, that can be controlled by a remote device, and can take multiple samples over a period of time.

SUMMARY OF THE INVENTION

The present invention is a sampling apparatus that allows multiple uncontaminated samples to be taken from hydrothermal vents and the oceanic or limnological water column. In its most basic form, the apparatus includes a sampling nozzle for taking in the sample. A sample collection unit is in fluid communication with the sampling nozzle and includes at least one sampling module for the collection of a predetermined type of sample. A fluid intake module is in fluid communication with the sample collection unit and the sampling nozzle. The fluid intake module includes at least one pump for drawing a sample fluid through the sampling nozzle and sample collection unit. Finally, a control module is in electrical communication with the fluid intake module. The control module includes a micro-controller for controlling the fluid intake module and a computer readable memory for storing sampling data for use by a user.

In operation, the sampling nozzle is moved into a desired sampling location and the micro-controller sends a signal to said fluid intake module to initiate collection of a sample. The fluid intake module then draws the sample fluid through said sampling nozzle and into said sample collection unit. The sampling module then stores a sample and the electronic controller stores the sampling data in memory for use by a user.

In the preferred embodiment, the sampling unit includes six removable sampling modules having an assembled series of interchangeable filter units and containers for collection of particulate or water samples. The preferred fluid intake module includes a distribution valve and two microgear pumps that act to take in samples through the sampling nozzle and an associated umbilical that permits uncontaminated sampling of the environment by manipulator arm or direct mounting on the vehicle. The preferred sampling nozzle includes a plurality of fluid inlets each sealed by individual end caps. The preferred nozzle also includes a temperature probe to permit continuous measurement of temperature at the site of sampling and a heat exchanger for preventing overheating of the umbilical by a sample.

Therefore, it is an aspect of the present invention to provide a sampling apparatus that is capable of obtaining uncontaminated samples of underwater hydrothermal vent microorganisms and/or microorganisms inhabiting the oceanic or limnological water column.

It is a further aspect of the present invention to provide a sampling apparatus that is capable of obtaining uncontaminated samples of underwater hydrothermal vent water.

It is a further aspect of the present invention to provide a sampling apparatus that is capable of obtaining uncontaminated samples from the oceanic or limnological water column.

It is a further aspect of the present invention to provide a sampling apparatus that may be operated from a remote site.

It is a further aspect of the present invention to provide a sampling apparatus that is capable of withstanding temperatures of up to 400° C.

It is a further aspect of the present invention to provide a sampling apparatus having a sterilizable sampling unit that collects multiple samples.

It is a further aspect of this invention to provide a sampling apparatus having sampling units with interchangeable male and female ends allowing units to be stacked.

It is a further aspect of this invention to provide a sampling apparatus that may be monitored electronically to provide an estimate of pumping rate, total volume of sample filtered and of the flow resistance of sample passing through the filters.

It is a further aspect of the present invention to provide a sampling apparatus that allows a temperature at the sampling site to be monitored.

It is a further aspect of the present invention to provide a sampling apparatus having a plurality of nozzles with removable caps that will allow multiple uncontaminated samples to be taken.

It is a further aspect of the present invention to provide a sampling apparatus utilizing an umbilical having a sample line heat exchanger incorporated inside.

Another aspect of the present invention is to provide a sampling apparatus in which an electronic controller/data collector monitors, controls and records sampling, and monitors and records temperature.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE DRAWINGS

The present invention is a sampling apparatus capable of conducting uncontaminated sampling of underwater hydrothermal vent microorganisms and water microorganisms, and/or microorganisms inhabiting the oceanic or limnological water column.

Figure 1:
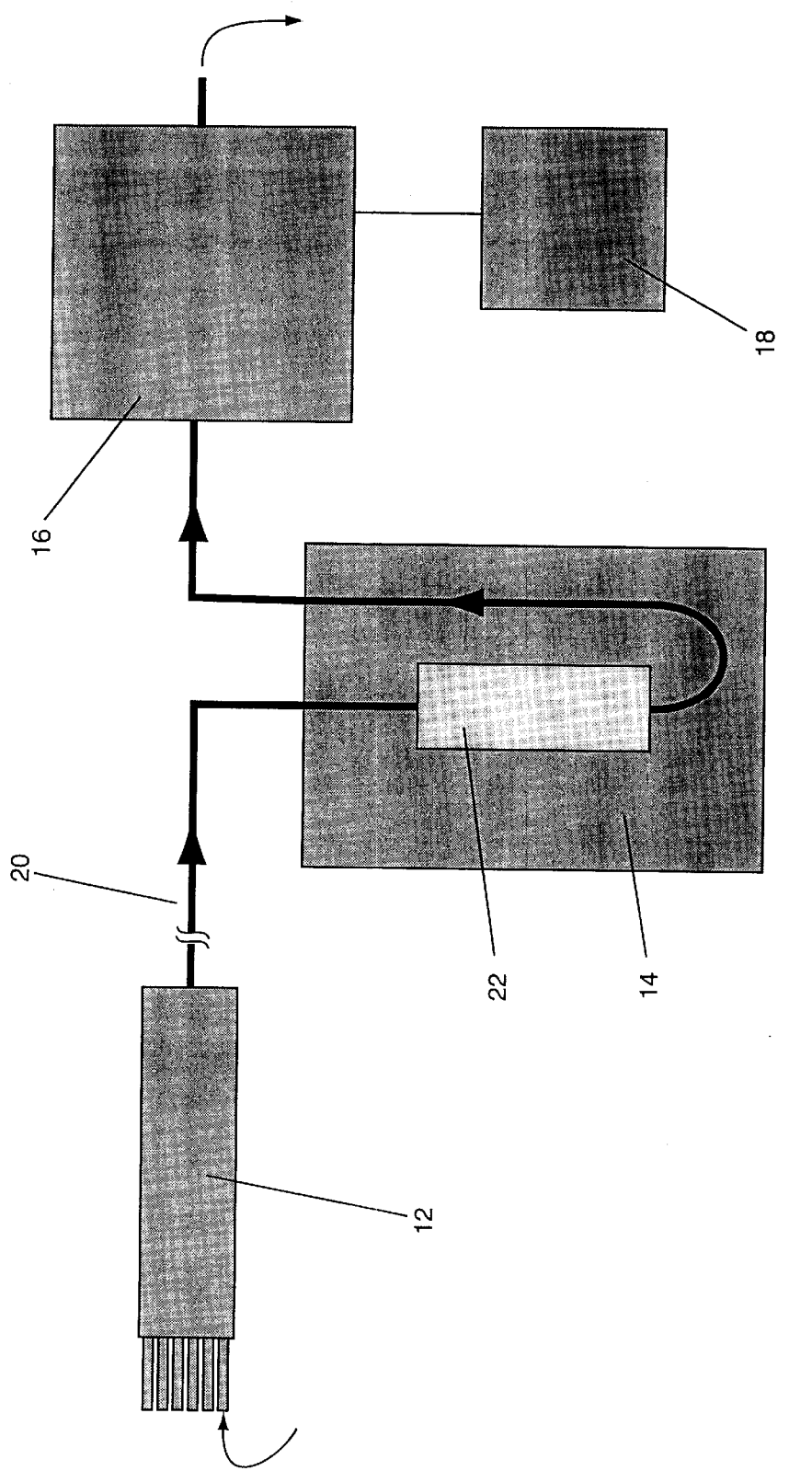
FIG. 1 is a block diagram of the basic sampling apparatus of the present invention.

As shown in FIG. 1, the apparatus 10 includes a sampling nozzle 12 and a sample collection unit 14 remotely coupled to the sampling nozzle 12 via an umbilical 20. Within the sample collection unit 14 is at least one sampling module 22 made up of an assembled series of interchangeable filter units and/or containers for collecting participate and/or water samples. A fluid intake module 16 is connected to the sample collection unit 14 and the sampling nozzle 12 and draws sample fluid through the apparatus 10. Finally, a control module 18 controls the operation of the fluid intake module 16 and provides an interface with the user.

In operation, the sampling nozzle 12 will be moved into a desired sampling location via a manipulator arm or, in cases where the nozzle is directly mounted to the underwater vehicle, via movement of the vehicle, or during hydrocast sampling by ship via hydrowire. The control module 18 then sends a signal to the fluid intake module 16 to initiate collection of a sample. The fluid intake module 16 draws sample fluid through the sampling nozzle 12 and umbilical 20 and into the sample collection unit 14, where a sample is collected within a sampling module 22. The remaining sample fluid within the apparatus 10 is subsequently drawn through the fluid intake module 16 and is exhausted out of the apparatus 10.

Figure 2:
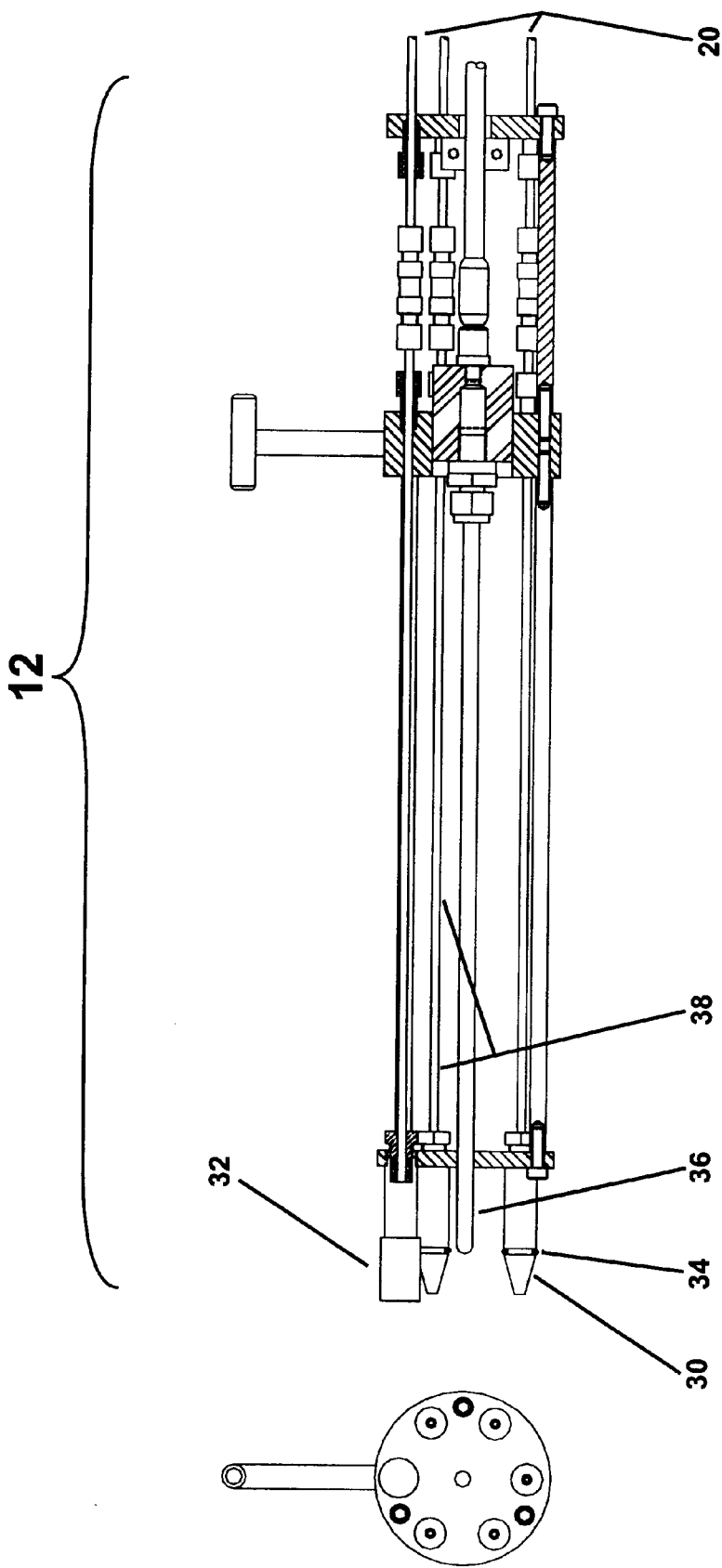
FIG. 2 is a side view of the preferred sampling nozzle of apparatus of the present invention.

As shown in FIG. 2, the preferred sampling nozzle 12 includes a plurality of inlet tubes 30 to which a plurality of disposable end caps 32 are removably mounted to the each of the inlet tubes 30. During the procurement cycle of each sample, an individual end cap 32 is removed due to the developed hydraulic pressure. This insures that the sample is protected from microbial and genetic contamination from the nozzle 12 surfaces. The preferred end caps 32 and inlet tubes 30 are made of a high temperature, sterilizable material, such as titanium, with the end caps 32 preferably sealed in place over the inlet tubes 30 via O-rings 34. These O-rings 34 are preferably made of a heat resistant perfloureoelastomer, such as KALREZ®, which have temperature tolerances near 400° C. and act to prevent fluid from coming in contact with the inlet tubes 30 prior to sampling. This arrangement provides very good protection from cross contamination while maintaining mechanical simplicity, which is a very important consideration for assuring reliable functioning of the device during remote operation in harsh environments.

The preferred sampling nozzle 12 also includes a temperature probe 36 for measuring the temperature of the sample fluid and communicating this temperature to the control module 18, where it is viewed and stored for future retrieval by a user. The temperature probe 36 may be a high temperature thermocouple, inductive temperature probe, or other art recognized probe for measuring high temperatures in undersea environments. In the preferred embodiment the temperature probe 36 is a platinum resistive temperature ("PRT") sensor with a nominal impedance at 0° C. on the order of 1000 Ohms to reduce the effects of resistance in the umbilical. An example of such sensor is the OMEGA W2142 or OMEGA W2152, manufactured by Omega Engineering of Stamford, Conn. The effective temperature range of the named devices is −50 to +600° C. The PRT element can be mounted at the sealed end of a titanium tube and maintained in thermal contact with the tube wall with a heat conductive paste. The opposite end of the tube will terminate in a pressure resistant under water connector. The PRT leads can be electrically isolated from the tube walls by heat resistant ceramic bead insulators (e.g., OMEGA thermocouple insulators having service temperatures to 1650° C.)

It is also preferred that the nozzle 12 include heat exchangers 38 for reducing the temperature of the sample fluid prior to its passing through the umbilical 20. By utilizing such a heat exchanger within the nozzle, it is possible to manufacture the umbilical from a plastic tubing, such as PEEK® tubing (temperature tolerance 250° C., continuous) without risk of thermal destruction in the event of exposure to very hot water during sampling. However, it is understood that other embodiments may utilize a heat resistant umbilical, eliminating the need for such a heat exchanger. In the simplest embodiment the heat exchanger is an extension of the sampling tubes 30 to where they are in contact with lower temperature (3–25° C.) water of the surrounding environment. The sample is cooled by conduction and convection of heat from the tubes into the surrounding water. Convection may be improved by using cooling fins or by coiling of the tubes 38 within the heat exchange section of the nozzle 12.

Figure 3:
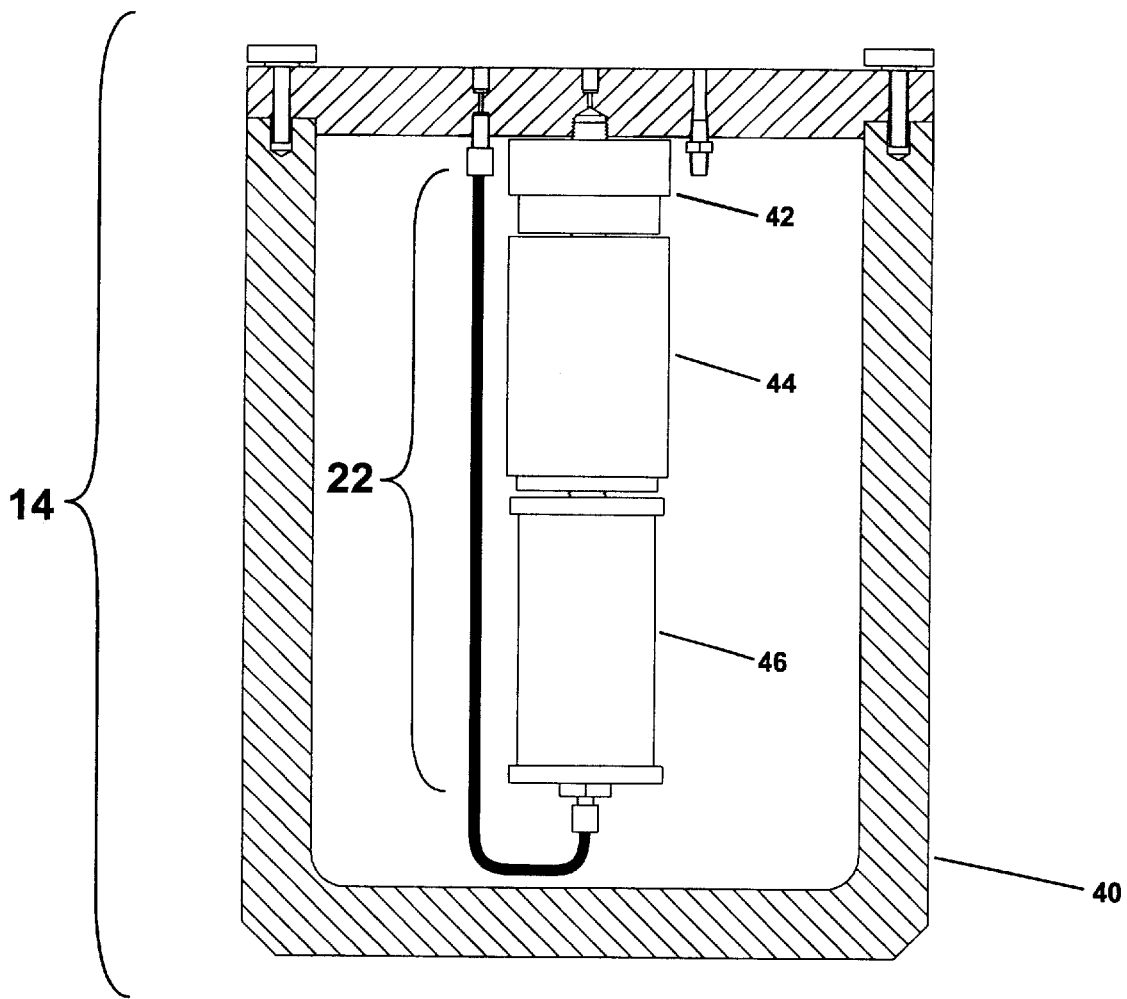
FIG. 3 is a side view of the preferred sample collection unit of the present invention in which the insulating housing has been cut away to reveal one sampling module.

As noted above, the sample collection unit 14 accepts the sample fluid from the sampling nozzle 12 and stores the desired samples for later analysis. As shown in FIG. 3, the sample collection unit 14 includes an insulating housing 40, and at least one removable sampling module 22.

The preferred insulating housing 40 is manufactured from a high density polyethylene (HDPE) to protect cold collected samples from large temperature excursions during retrieval of the apparatus through warm waters above the thermocline. It is preferred that the insulating housing be manufactured of a 1 inch thick layer of HDPE, which results in an approximately 6° C. rise in internal temperature if the unit were exposed to 25° C. surface waters for 1 hour. However, by incorporating additional sheets of ½ inch SYNTACTIC foam into the insulating box, the internal temperature rise of the box may be limited to less than 3° C. under the same conditions.

In the preferred sampling apparatus 10, six sampling modules 22 are mounted within the insulating housing 40 to allow up to six samples to be taken. Each of the sampling modules 22 preferably includes a series of interchangeable male and female ends that will allow the units to be stacked in line in various ways according to user sampling needs. As shown in FIGS. 3–6, the preferred sampling module 22 can consist of any assemblage of a single filter unit 42, high capacity filter unit 44, and/or fluid sample vessel 46.

Figure 4:
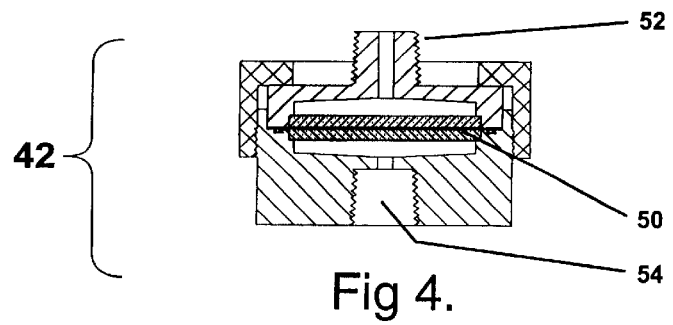
FIG. 4 is a cut away side view of the single filter unit of the sampling module as shown in FIG. 3.

The single filter unit 42, shown in detail in FIG. 4, includes a single filter 50 disposed between a fluid inlet 52 and fluid outlet 54. The material from which filter 50 is manufactured will vary depending upon the type of particulate material to be collected. For example, where microbial samples are to be collected, filter 50 will preferably be manufactured of a commercially available 47 millimeter filter, while the filter 50 may be manufactured of NYTEX® (Tetko, Inc. of Briarcliff Manor, N.Y.) screening where the collection/removal of higher forms, such as larvae, are required. Other possible filter 50 materials made by a number of manufactures that can be used with the filter units 42, 44 include polycarbonate filters, glass fiber filters, cellulose filters, nylon filters, etc.

Figure 5:
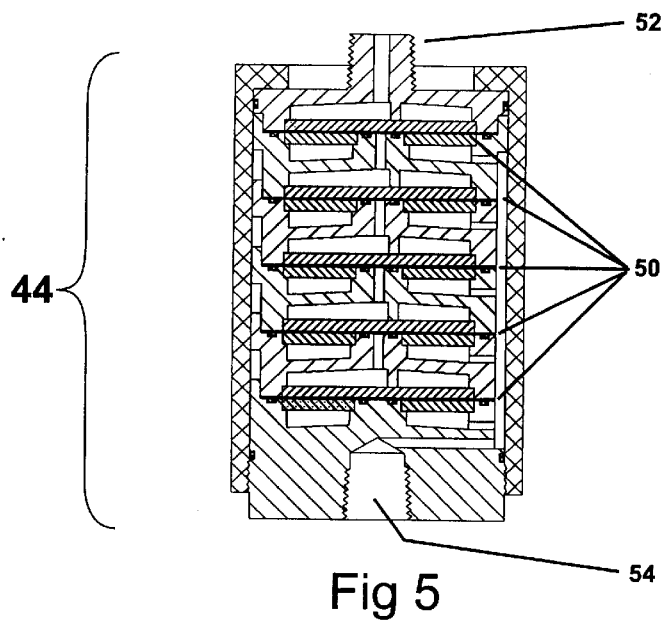
FIG. 5 is a cut away side view of a high capacity filter unit of the sampling module as shown FIG. 3.

The high capacity filter unit 44, shown in detail in FIG. 5, also includes a fluid inlet 52 and fluid outlet 54, and preferably incorporates parallel filters 50 that provide a combination of increased particulate capacity and convenient removal. As was the case with the single filter unit 42, the materials from which the filters 50 in the high capacity filter unit 44 are manufactured will vary, depending upon particular application, but are preferably the same 47 mm filter materials or NYTEX® screening described with reference to the single filter unit 42

Figure 6:
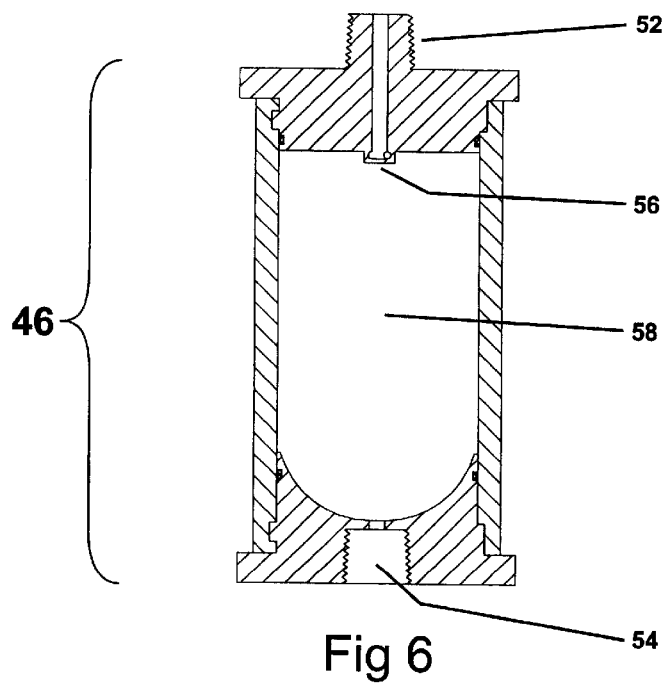
FIG. 6 a cut away side view of the fluid sample vessel of the sampling module as shown in FIG. 3.

The fluid sample vessel 46, shown in detail in FIG. 6, obtains filtered or unfiltered water samples by flushing out sterile, DNA free seawater with a sufficient volume of sample to be representative of the environment. The preferred vessel 46 includes a fluid inlet 52 having a low sheer ducted nozzle 56 that directs the fluid into the sample chamber 58 in a spiral motion to effect complete mixing within the sample chamber 58 as quickly as possible. In the preferred embodiment, the samples collected within the vessel 46 approximate the following model: $(S_V) \approx S_E(1-e^{-kv})$, where $S_V$ is the concentration of sample after volume V has been pumped through the vessel, $S_E$ is the concentration of the sample in the environment and k is an experimentally determined dilution constant. This algorithm is incorporated into the display software and provides an estimate of a Sample Vessel Exchange Percentage $(S_V/S_E) \times 100$ so the user knows when a representative sample from the environment has been taken. If an increment of sample (V) is introduced into a fluid containing vessel of constant volume, instantly mixed with the resident fluid and an equal increment of the mixed fluid simultaneously removed, the concentration of sample within the vessel will follow the model $(S_V)=S_E(1-e^{-kv})$. The purpose of the ducted nozzle is to introduce sample into the vessel so that it mixes with the resident fluid as completely and quickly as possible so that the model is reasonably obeyed. Low sheer is desirable so that particle size distribution is not disrupted should unfiltered aqueous samples be collected.

The preferred sample collection unit 14 is completely removable from the apparatus 10 and is manufactured of a material that is compatible with sterilization procedures that would be implemented for the destruction of vent microorganisms and their DNA. Because elimination of hyperthermophiles may require autoclaving schedules that extend beyond classically used procedures, construction materials were chosen that were completely stable to temperatures greater than 120° C. Further, as DNA is not reliably destroyed by autoclaving, surfaces in contact with sample must also undergo sequential exposure to 0.5 N acid, which depurinates nucleic acid, and to 0.5 N base containing 1.5 N NaCl, which results in the alkaline catalyzed hydrolysis of the phosphodiester backbone. A possible sterilization scenario might entail autoclaving, treatment with acid, treatment with base and a second autoclaving. Rinsing and final filling of the apparatus would be effected with sterile DNA-free (e.g., UV exposed) distilled water and (if sampling the marine environment) seawater, respectively.

The preferred material to meet the sterilization requirements is polysulfone plastic. Polysulfone is a biologically inert plastic that is thermally stable to temperatures up to 165° C., and is unaffected by exposure to acids, bases and polar alcohols. The plastic is optically clear, possesses good machining characteristics and relatively low water absorption (less than 0.5%). Accordingly, the use of this material is preferred not only for its sterilizbility, but also due to the ability to visualize samples through it, its ease of fabrication, and its dimensional stability when used in aquatic environments.

As noted above, the fluid intake module 16 accepts an instruction from the control module 18 and initiates the sampling process. In the preferred embodiment, described in detail with reference to FIGS. 7–9, the fluid intake module 16 includes a pair of pumps 60, 62 and a twelve port distribution valve 64 connected to the pre-sterilized, DNA-free sample collection unit 14 by sterile Teflon® or Peek® tubes 66, 68.

The preferred distribution valve 64 (FIG. 7) includes a rotor and stator assembly that is driven by a bi-directional stepping motor 90 coupled to a 50:1 gear head 92. The position of the rotor 93 is measured using a magnetic encoder 95 which permits automatic alignment of the rotor and stator assembly. It is preferred that the rotor and stator assembly include a polysulfone stator 97 and KYNAR® rotor 78, which are sealed by a wave spring/bearing compression assembly 103. Polysulfone is the preferred material for the valve stator because of its sterilizability, resistance to DNA removal treatments and dimensional stability. An inert fluroplastics such as KYNAR® is preferred for the valve rotor because in addition to its sterilizability and chemical inertness the material permits a low friction seal with the stator.

The preferred pumps 60, 62 are positive displacement, graphite microgear pumps driven by three-phase brushless DC motors via a magnetic coupling created by a magnet. It is preferred that these pumps be pressure compensated by immersion in oil, and the speed of the motor capable of electronic monitoring to provide an accurate estimate of total volume of sample filtered and of the flow resistance (pressure differential) of sample passing through the filters. These pumps 60, 62 are connected to a cap removal outlet 70 and a sample inlet 72 in the distribution valve 64. They communicate with each of the six cap removal ports 74 and with each of the six sampling modules 22 of the sampling unit 14 via six sampling ports 76 in the distribution valve 64.

Figure 7:
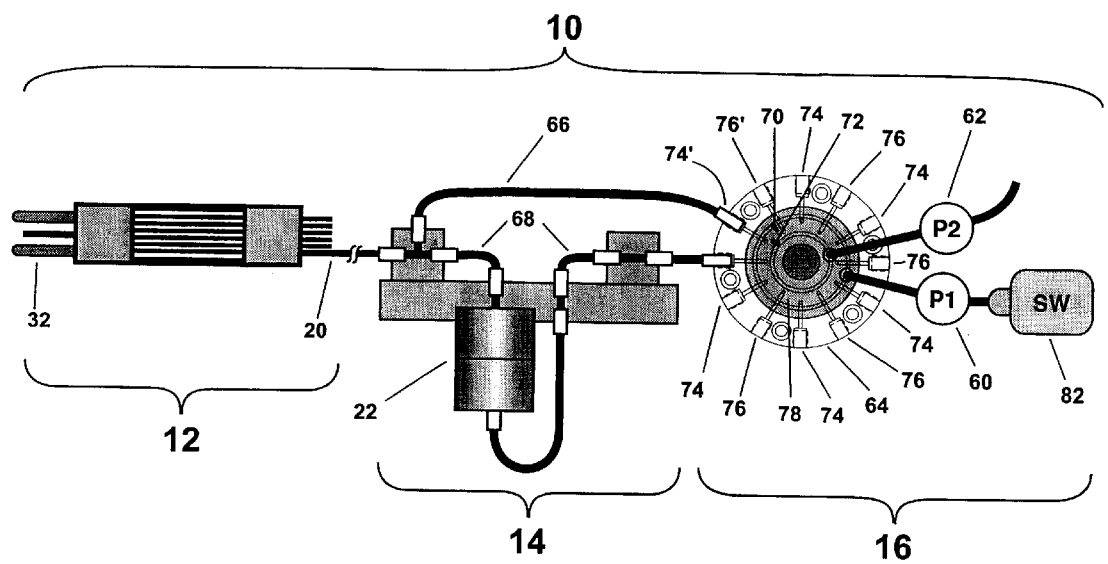
FIG. 7 is a functional diagram of the sampling apparatus of the present invention showing the fluid distribution valve in its pre-sampling position and an engineering drawing of the fluid distribution valve.
Figure 7:
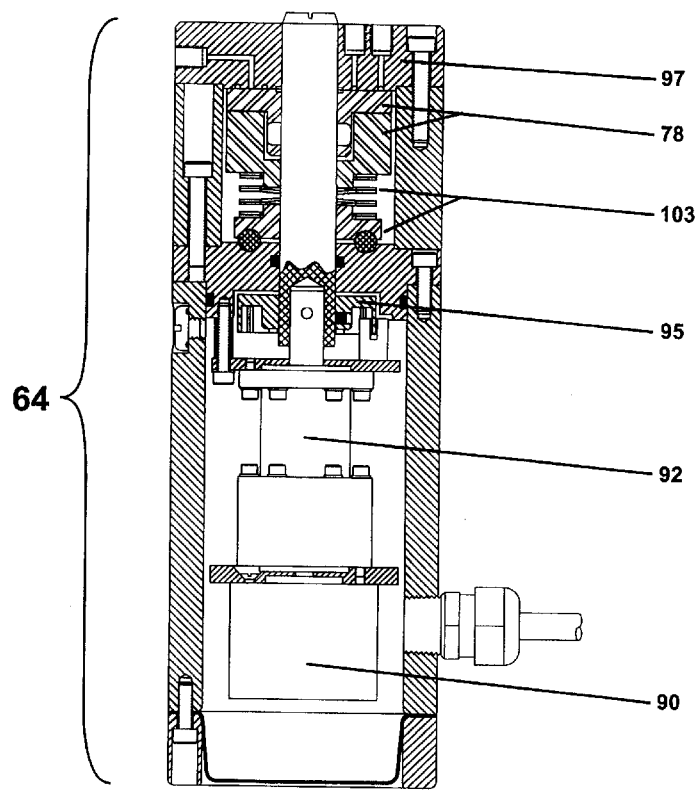
Figure 8:
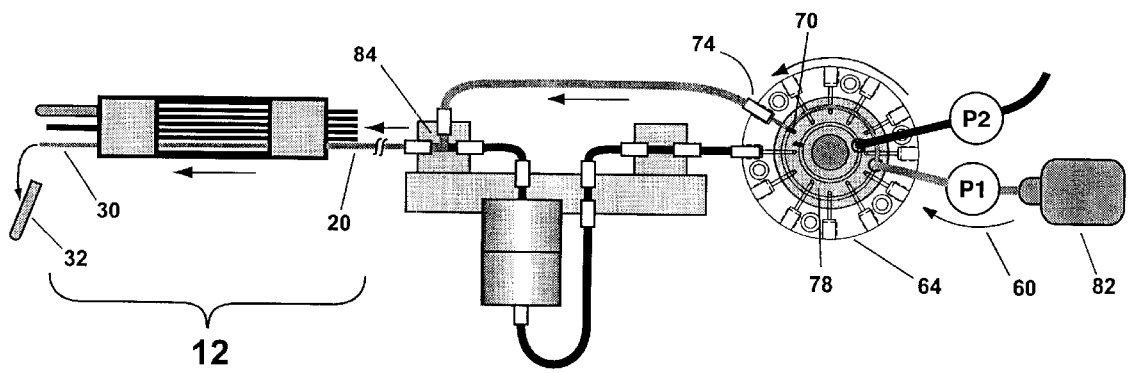
FIG. 8 is a functional diagram of the sampling apparatus of the present invention showing the fluid distribution valve in its cap removal position, a cap being removed, and showing (in gray) the path taken by the sterile water during cap removal.
Figure 9:
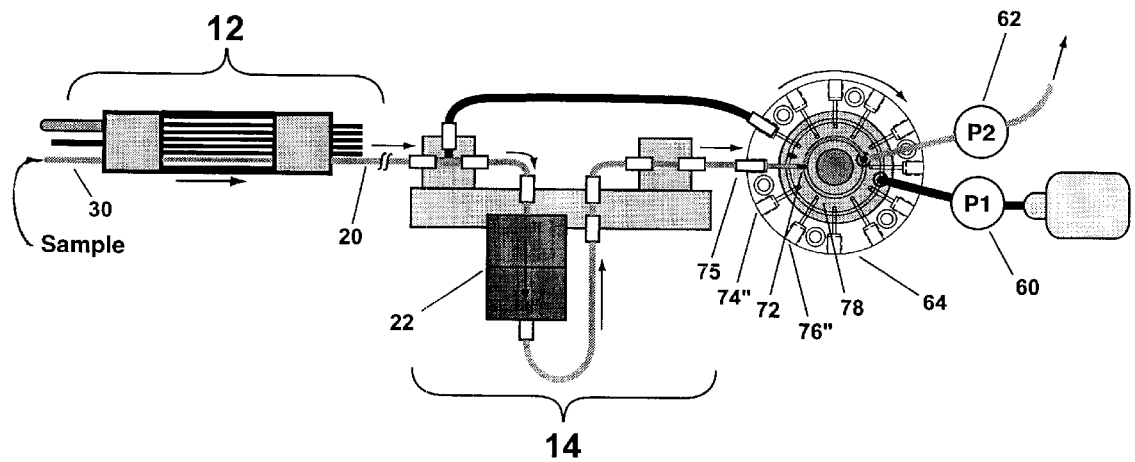
FIG. 9 is a functional diagram of the sampling apparatus of the present invention showing the fluid distribution valve in its sampling position and showing (in gray) the path taken by the sample fluid.

Referring to FIGS. 7–9, the method of collecting samples via the preferred apparatus 10 is described. FIG. 7 shows the apparatus 10 between sampling events. In this arrangement, the rotor 78 of the distribution valve 64 is positioned such that the cap removal outlet 70 and the sample inlet 72 are between the cap removal port 74' and the previous sampling port 76', effectively sealing the valve.

As shown in FIG. 8, the first sampling event is initiated by advancement of the rotor 78 such that the cap removal outlet 70 of the distribution valve 64 is aligned with the cap removal port 74. The cap removal pump 60 then pumps sterilized, DNA-free, water from a sterile water reservoir 82 through the valve to a sampling line "T" manifold 84 and umbilical 20 to sampling nozzle 12. The pressure developed hydraulically removes the disposable end cap 32 to expose a sterile inlet tube 30. Once the end cap has been removed the cap removal pump 60 is turned off.

As shown in FIG. 9, once the cap removal pump 60 is turned off, the rotor 78 of the distribution valve 64 is advanced such that the sample inlet 72 is aligned with a sampling port 75. Sample collection is then initiated by activating the sampling pump 62, which draws a sample through the sterile inlet tube 30 of sampling nozzle 12 to the sampling module 22 of the sample collection unit 14 where a sample is taken. Once the sample is taken, the remaining sample fluid is pumped through the distribution valve 64, to the sampling pump 62, which exhausts it back into the environment.

Once the sample has been taken, the sampling pump 62 is turned off, the distribution valve 64 is advanced to the next sealed position between sampling port 76" and cap removal port 74". This process is then repeated for each of the remaining samples beginning with the sample taken through sampling port 76".

Samples contained within the sampling module 22 are protected from contamination by a long diffusion path in the umbilical 20 and by the sealed distribution valve 64. A check valve is not normally implemented on the sample inlet side of the sampling module 22 to preserve particle size integrity, but other embodiments may include such a check valve.

Figure 10:
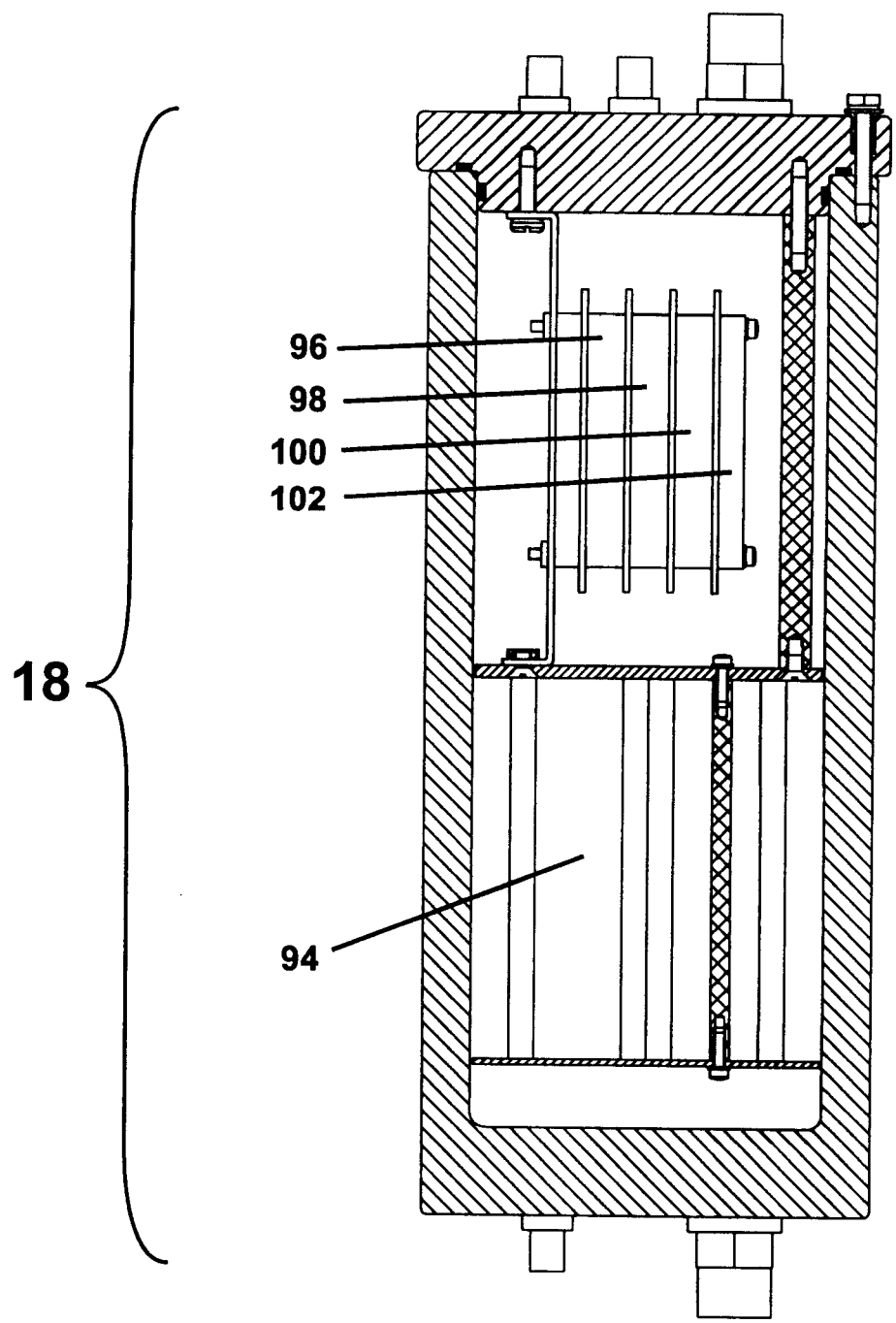
FIG. 10 is a functional diagram of the electronic controller of the present invention showing component computer, pump and valve driver circuit boards, data acquisition circuit board, and battery pack.

The preferred control module 18 (FIG. 10) is a combination electronic controller/ data recorder for controlling sampling events and interfacing with the user. The preferred control module 18 includes four printed circuit boards and a battery pack 94. One printed circuit board is a TATTLE-TALE 8 single board micro-controller 96, manufactured by Onset Computer Corporation of Bourne, Mass. The microcontroller runs a control program that sends instructions to, and receives data from, the sampling apparatus through three peripheral driver boards designed and built by the inventors.

The first of these peripheral driver boards is an auxiliary/ stepper motor driver 98 containing hardware that converts pulse trains generated by the TATTLETALE 8 microcontroller 96 into the commutation signals that drive a stepper motor 90 to rotate the rotor 78 of the distribution valve 64. The board also permits the automatic registration of the rotor and stator assembly of the distribution valve 64 by seeking and finding a "home port". The auxiliary portion of the board includes a battery voltage monitoring circuit and a resistive temperature measurement circuit from the temperature sensor.

The remaining two boards are 3-phase motor controller boards. The first motor controller board 100 is associated with the cap removal pump 60, and the second motor controller board 102 is associated with the sampling pump 62. On/Off and motor speed control are communicated through these boards to the pump motors via a high-speed serial connection from the TATTLETALE 8 microcontroller 96. Hall effect sensors mounted in the preferred motor also permit the determination of pump motor speed, which can be used for regulating the rate of filtration and determining the volume of sample filtered.

The preferred control program allows the apparatus to run in one of three possible modes; manual, semiautomatic, and time series. Manual and semiautomatic modes require interaction with the user, either in submersible, remotely operated vehicles, or autonomous underwater vehicles. In these modes, the apparatus is activated by the user. In the time series mode, all functions are automated.

Upon activation, the control module 18 adjusts the initial pumping (filtration) rate to a preprogrammed value. The user is presented with a display, updated every second, showing elapsed time, temperature, filtration rate, total volume pumped, Sample Vessel Exchange Percentage, and battery voltage. In the manual mode, the user decides when to terminate sample collection, unless occlusion of the filter results in a reduction in the flow rate to below a preset value. If this minimum is reached, the pump is turned off automatically and prevents the filtered samples from being subjected to an excessive pressure differential. The semiautomatic mode retains the above functions but will, in addition, automatically turn off the pump when a preset volume of sample has been filtered. In the time series mode, all functions are automated. Sample collection begins at a preset time, programmed by the user, and is terminated according to the same criteria as in the semiautomatic mode. Regular or irregular intervals between samples are programmed into the instrument prior to deployment.

In all modes, a time history of sample site temperature, volume of sample pumped, Sample Vessel Exchange Percentage, battery voltage, and elapsed time are recorded in solid state memory at user determined intervals to provide a history of the sampling process. Upon completion of sampling, a data file containing the volume pumped, estimated Sampling Vessel Exchange Percentage, mean and standard deviation of probe temperatures, start and stop times, ports used, initial and final battery voltages, and other diagnostic messages are stored both in RAM and in nonvolatile flash memory for later use.

The preferred embodiment of the control module also includes a software interface to allow the user to control the apparatus via a layered menu structure. From the main menu, the operator has access to the real-time clock, system diagnostic and test routines, deployment programming and control, and the instrument data file. The user is presented with the main menu when the sampler is first powered up and can return to the main menu anytime. Components of the main menu preferably allow the user to set the time, perform diagnostics, test operation, deploy the system, off-load data, and sleep.

The "set time" option permits the operator to set the real time clock of the Tattletale 8 micro-controller. The "diagnostics" option displays main battery voltage and temperature sensor until terminated by the operator. This option is useful during bench testing, when calibrating the temperature sensor, and to monitor the temperature during the positioning of the probe for sample collection (e.g., positioning into a warm water flow in a hydrothermal vent).

The "manual operation" option allows direct control of the pumps and valve by the operator. This option is intended primarily for bench use during system testing and preparation prior to deployment. The desired sample volume, flow rate, minimum flow rate, pumping time limit, and pump direction can be set for each of the two pumps from this menu. Pump parameters such as flow rate, cumulative volume, elapsed time, estimated Sample Vessel Exchange Percentage, and probe temperature are monitored and displayed at one-second intervals during operation. The final volume and elapsed time are displayed when the operation is concluded. During any pumping operation, the flow and elapsed time are displayed when the operation is concluded and the flow rate is monitored and dynamically adjusted by a closed loop control algorithm. The pumping rate is tracked by the control algorithm and adjusted when necessary to protect the integrity of the sample. The valve can be commanded to any of the cap removal or sample ports from the manual operation menu. Individual port numbers can be selected arbitrarily or the position can be incremented or decremented via a single port. The current port number is displayed during and after each rotation.

The "deploy system" option allows the operator to choose from several different modes of operation. For example, pump parameter settings (total volume pumped, initial flow rate, filtration time limit) can be set as a default for all samples or individually adjusted between each sample. A given sampling event is initiated by a single keystroke. Valve position is automatically incremented for each sampling event (normal operation) or can be advanced manually.

The "offload data" option provides data file recovery from the instrument in ASCII text format using the "capture to file" capability of the terminal emulator running on the user's PC. Finally, the "Sleep" option of the Main Menu places the Apparatus in a low power mode to extend battery life.

The preferred communications interface is a standard three wire RS-232 connection passing standard ASCII characters. The user is normally an investigator working through a laptop PC running a terminal emulator. This interface can also be controlled by a supervisory microprocessor such as might be used to coordinate the actions of an Autonomous Underwater Vehicle.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed:

1. A sampling apparatus for collecting samples from underwater hydrothermal vents, and the oceanic or limnological water column said apparatus comprising:
   a sampling nozzle-comprising a plurality of inlet tubes;
      an end cap removably attached to each of said plurality of inlet tubes such that contamination of said inlet tubes is prevented;
      a sample collection unit in fluid communication with sampling nozzle, said sample collection unit comprising at least one sampling module for the collection of a predetermined type of sample;
      a fluid intake module in fluid communication with said sample collection unit and said sampling nozzle, said fluid intake module comprising at least one pump for drawing a sample fluid through said sampling nozzle and said sample collection unit; and
      a control module in electrical communication with fluid intake module, said control module comprising a micro-controller for controlling said fluid intake module and a computer readable memory for storing sampling data for use by a user;
      wherein said sampling nozzle is moved into a desired sampling location, said micro-controller sends a signal to said fluid intake module to initiate collection of a sample, said fluid intake module draws the sample fluid through said sampling nozzle and into said sample collection unit, said sampling module stores a sample, and said computer readable memory stores sampling data for use by a user.

2. The sampling apparatus as claimed in claim 1 wherein said sampling nozzle further comprises a temperature probe for measuring a temperature of said sample fluid.

3. The sampling apparatus as claimed in claim 1 wherein said sampling nozzle is connected to said sample collection unit via a flexible umbilical, and wherein said sampling nozzle further comprises a heat exchanger for reducing the temperature of the sample fluid.

4. The sampling apparatus as claimed in claim 1 wherein said sample collection unit further comprises an insulating housing disposed about said at least one sampling module.

5. The sampling apparatus as claimed in claim 1 wherein said at least one sampling module comprises at least one stage chosen from a group consisting of a filter unit and a fluid sample vessel.

6. The sampling apparatus as claimed in claim 5 wherein said predetermined type of sample is a particulate sample and wherein said at least one stage is a filter unit.

7. The sampling apparatus as claimed in claim 6 wherein said filter unit is chosen from a group consisting of a single filter unit and a high capacity filter unit.

8. The sampling apparatus as claimed in claim 5 wherein said predetermined type of sample is a fluid sample and wherein said at least one stage is a fluid sample vessel.

9. The sampling apparatus as claimed in claim 8 wherein said fluid sample vessel comprises a fluid inlet having a low sheer ducted nozzle dimensioned to direct the sample in a spiral motion to effect more rapid and complete mixing of the sample.

10. The sampling apparatus as claimed in claim 1 wherein said sampling module is manufactured of polysulfone plastic.

11. The sampling apparatus as claimed in claim 1 wherein said fluid intake module comprises a sampling pump, a cap removal pump, and a distribution valve in fluid communication with said sampling pump and said cap removal pump.

12. The sampling apparatus as claimed in claim 11 wherein said distribution valve comprises a rotatable rotor having a cap removal outlet in fluid communication with said cap removal pump and a sample inlet in fluid communication with said sampling pump.

13. The sampling apparatus as claimed in claim 12 further comprising a sterile water reservoir in fluid communication with said cap removal pump and a sampling line manifold terminating in a cap removal port, wherein said rotatable rotor may be rotated to align said cap removal port with said cap removal outlet such that said sterile water reservoir is in fluid communication with said sampling line manifold.

14. The sampling apparatus as claimed in claim 12 wherein said control module is programmed to automatically rotate said rotatable rotor of said distribution valve.

15. The sampling apparatus as claimed in claim 11 wherein said cap removal pump and said sampling pump are microgear pumps.

16. The sampling apparatus as claimed in claim 11 wherein said control module is programmed to automatically control said cap removal pump and said sampling pump.

17. The sampling apparatus as claimed in claim 1 wherein said control module further comprises a software program stored upon said computer readable memory and executable by said micro-controller to provide a software interface to allow the user to control said apparatus.

18. The sampling apparatus as claimed in claim 17 wherein said software interface comprises a main menu allowing the user to perform at least one function chosen from the group consisting of setting a real time clock, performing diagnostics, testing operation of said apparatus, deploying said apparatus, offloading data from said apparatus, and suspending operation of said apparatus.

19. The sampling apparatus as claimed in claim 17 wherein said software program allows said apparatus to run in a mode selected from a group consisting of manual mode, semiautomatic mode, and time series mode.

* * * * *